US006787356B1

(12) United States Patent
Studer et al.

(10) Patent No.: US 6,787,356 B1
(45) Date of Patent: Sep. 7, 2004

(54) CELL EXPANSION SYSTEM FOR USE IN NEURAL TRANSPLANTATION

(75) Inventors: Lorenz Studer, New York, NY (US); Ron D. McKay, Bethesda, MD (US)

(73) Assignee: The United States of America as represented by the Department of Health and Human Services, Washington, DC (US)

(*) Notice: Subject to any disclaimer, the term of this patent is extended or adjusted under 35 U.S.C. 154(b) by 0 days.

(21) Appl. No.: 09/744,384

(22) PCT Filed: Jul. 23, 1999

(86) PCT No.: PCT/US99/16825
§ 371 (c)(1),
(2), (4) Date: Mar. 16, 2001

(87) PCT Pub. No.: WO00/05343
PCT Pub. Date: Feb. 3, 2000

Related U.S. Application Data

(60) Provisional application No. 60/093,991, filed on Jul. 24, 1998.

(51) Int. Cl.$^7$ .......................... C12N 5/02; A61K 48/00

(52) U.S. Cl. ...................... 435/377; 435/325; 435/384; 424/93.21; 514/44

(58) Field of Search ............................... 435/377, 324, 435/384, 325; 924/93.21; 514/44

(56) References Cited

U.S. PATENT DOCUMENTS

| | | | |
|---|---|---|---|
| 5,218,094 A | * | 6/1993 | della Valle .................. 530/417 |
| RE35,653 E | | 11/1997 | Aebischer et al. |
| 5,750,103 A | | 5/1998 | Cherksey |
| 5,753,491 A | | 5/1998 | Major et al. |
| 5,792,900 A | | 8/1998 | Lee et al. |
| 5,853,385 A | | 12/1998 | Emerich et al. |
| 5,869,463 A | | 2/1999 | Major et al. |
| 5,874,301 A | | 2/1999 | Keller et al. ................. 435/325 |

FOREIGN PATENT DOCUMENTS

| | | |
|---|---|---|
| WO | WO 91/09936 | 7/1991 |
| WO | WO 94/10292 | 5/1994 |
| WO | WO 94/16718 | 8/1994 |
| WO | WO 96/15224 | 5/1996 |

OTHER PUBLICATIONS

Verma et al (1997) Nature 389:239–242.*
Palu et al (1999) J. Biotechnol. 68: 1–13.*
Fox, ASM News, Feb. 2000, 66 (2): 1–3.*
Deloulme et al (1991) J. Neuroscience Research 29:499–509.*
Björkland (2000) Neural transplantation in neurodegenerative disease. Wiley, Chichester (Novartis Foundation Symposium) p. 7–20.*
Svendsen et al (1999) TINS 22:357–364.*
Bohler et al (1999) Cells Tissues Organs 165:237–245.*
Buc–Caron (1995) Neurobiology of Disease 2:37–47.*
Eldridge et al (1987) Journal of Cell Biology 105:1023–1034.*
Debeir et al., Neuroscience, 1998, vol. 82, No. 3, pp. 739–752.*
Studer, L., "Culture of Substantia Nigra Neurons", *Current Protocols in Neuroscience*, vol. 1, Unit 3.3, pp. 3.3.1–3.3.12 (1997).
Bottenstein et al. "Growth of a Rat Neuroblastoma Cell Line in Serum–Free Supplemental Medium", *Proc. Nat'l. Acad. Sci.*, USA 75 (1979): pp. 514–517.
Studer, L. et al. "Transplantation of in Vitro Expanded and Reaggregated Mesencephalic Precursors to Behavioral Recovery in 60HDA Lesioned Rats," *Society for Neuroscience abstracts*, vol. 23, No. 1–2 (1997): pp. 1998. XP000870279.
Strecker et al. "Survival and Function of Aggregate Cultures of Rat Fetal Dopamine Neurons Grafted in a Rat Model of Parkinson's Disease," *Exp. Brian Res.*, vol. 76, No. 3 (1989): pp. 315–22. XP000867471.
Studer et al. "Transplantation of Expanded Mesencephalic Precursors Leads to Recovery in Parkinsonian Rats", *Nat. Neurosci.*, vol. 1, No. 4 (Aug. 1998): pp. 290–295. XP000870304.
Reynolds et al. "Generation of Neurons and Astrocytes from Isolated Cells of the Adult Mammalian Central Nervous System", *Science*, vol. 255 (Mar. 27, 1992): pp. 1707–1710.
Arsenijevic et al. "Insulin–Like Growth Factor–I Is a Differentiation Factor for Postmitotic CNS Stem Cell–Derived Neuronal Precursors: Distinct Actions from Those of Brain–Derived Neurotrophic Factor", *The Journal of Neuroscience*, vol. 18, No. 6 (Mar. 15, 1998): pp. 2118–2128.
Johe et l. "Single Factors Direct the Differentiation of Stem Cells from the Fetal and Adult Central Nervous System," *Genes & Development*, vol. 10 (1996): pp. 3129–3140.

(List continued on next page.)

*Primary Examiner*—Terry Mickelvey
*Assistant Examiner*—Nancy T. Vogel
(74) *Attorney, Agent, or Firm*—Merchant & Gould P.C.

(57) ABSTRACT

The invention provides a method of culturing cells which includes a proliferating step in which the number of precursor cells is expanded and a differentiating step in which the expanded precursor cells develop into neuronal cells. The proliferating step includes the step of incubating the precursor cells in proliferating medium which includes basic fibroblast growth factor (bFGF). The differentiating step includes incubating the precursor cells in differentiation media in a manner effective to form a cellular aggregate that is not adhered to any surface of the incubation vessel. In a preferred embodiment, the cells are incubated in a roller tube. The differentiation media can also include at least one differentiating agent. The invention also provides a method for treating a neurological disorder, such as Parkinson's disease, a method of introducing a gene product into a brain of a patient, an assay for neurologically active substances, and a cell culture.

23 Claims, 8 Drawing Sheets

OTHER PUBLICATIONS

Honegger et al. "Growth and Differentiation of Segregating Fetal Brian Cells in a Serum—Free Defined Medium", *Nature*, vol. 282 (Nov. 15, 1979): pp. 305–308.

Björklund, A. et al., "Cell replacement therapies for central nervous system disorders", *nature neuroscience*, vol. 3, No. 6, pp. 537–544 (Jun. 2000).

Clarkson, Edward D., et al., "Development of Fetal Neural Transplantation as a Treatment for Parkinson's Disease", *Life Science*, vol. 65, No. 23, pp. 2427–2437 (1999).

Olanow, C.W., et al. "Fetal nigral transplantation as a therapy for Parkinson's disease", *trends in Neurosciences*, vol. 19, No. 3, pp. 102–109 (1996).

Wartiovaara, K., "Gene Therapy Approaches to Neurodegenerative Disease", *Neural Notes*, vol. V, Issue 3, pp. 5–8, (2000).

Dambly–Chaudiere et al., "The bHLH genes in neural development," *Int. J. Dev. Biol.*, 42:269–273 (1998).

Skeath, J. et al., "The *achaete–scute* complex proneural genes contribute to neural precursor specification in the *Drosophila* CNS," *Current Biology*, 6(9):1146–1152 (1996).

* cited by examiner

CELL EXPANSION SYSTEM FOR USE IN NEURAL TRANSPLANTATION

This application claims priority to U.S. Provisional Application Serial No. 60/093,991, filed Jul. 24, 1998, entitled CELL EXPANSION SYSTEM FOR USE IN NEURAL TRANSPLANTATION, the disclosure of which is hereby incorporated by reference.

FIELD OF THE INVENTION

This invention relates to the use of differentiated cells in the treatment of neurodegenerative disorders.

BACKGROUND OF THE INVENTION

Parkinson's disease is a neurodegenerative disorder affecting an estimated one million patients in the United States. Several strategies are being pursued to develop new therapies for Parkinsonian patients. These techniques range from the use of dopaminotrophic factors (Takayama et al., (1995) *Nature Med.* 1, 53–58) and viral vectors (Choi-Lundberg et al., (1997) *Science* 275, 838–841) to the transplantation of primary xenogeneic tissue (Deacon et al., (1997) *Nature Med.* 3, 350–353). Fetal nigral transplantation is a clinically promising experimental treatment in late stage Parkinson's disease. More than 200 patients have been transplanted worldwide and clinical improvement was confirmed (Olanow et al. (1996) *Trends Neurosci.* 19, 102–109 and Wenning et al., (1997) *Ann.Neurol.* 42, 95–107) and was correlated to good graft survival and innervation of the host striatum in post mortem studies of transplanted patients (Kordower et al., (1995) *N.Engl.J.Med.* 332, 1118–1124).

Cell transplantation usually involves transplanting primary cells or immortalized cells into a patient. There has been mixed success in clinical trials where primary cells have been utilized. It is believed that the inadequate supply of primary cells or use of different proportions of primary cell types cause many trials to fail or to give inconsistent results.

Furthermore, neural transplantation remains a controversial procedure. Current transplantation treatment involves the use of material derived from at least 3–5 embryos to obtain a clinically reliable improvement in the patient. This poses an enormous logistical and ethical dilemma.

For these reasons, much effort has been devoted to finding alternatives to fetal tissue for use in transplantation. Although use of neural stem cells is promising because stem cells can be proliferated prior to differentiation, such stem cells have a relatively low proportion (about 0.1%) dopaminergic neurons. Since the clinical efficacy of transplants is in large part dependent upon the number of dopaminergic cells transplanted, finding a method to increase the proportion of dopaminergic cells in a CNS stem cell culture would have obvious clinical benefits. Additionally, successful numerical expansion of primary CNS precursors could alleviate some of the ethical and technical difficulties involved in the use of human fetal tissue. There is thus a need for a process that will provide sufficient viable cells for a reliable, effective clinical cell transplantation.

SUMMARY OF THE INVENTION

A first aspect of the invention provides a method of culturing cells. The method includes a proliferating step in which the number of precursor cell is expanded. The proliferating step includes the step of incubating the precursor cells in proliferating medium which includes basic fibroblast growth factor (bFGF). Preferably the precursor cells are obtained from a human fetal tissue between embryonic week 5 to embryonic week 8. The method also includes a differentiating step in which the expanded precursor cells develop into neuronal cells. The differentiating step includes incubating the precursor cells in differentiation media, wherein the cells are agitated during the incubation in a manner effective to form a cellular aggregate that is not adhered to any surface of the incubation vessel. In a preferred embodiment, the cells are incubated in a roller tube.

According to the invention, the differentiation media can also include at least one differentiating agent. Examples of differentiating agents include cyclic adenosine monophosphae (cAMP), dopamine, cAMP modulating agents and ascorbic acid. Preferably cAMP is N6,2-O-Dibutyrladenosine 3':5' Cyclic Monophosphate (dbcAMP) and/or 8-Bromoadenosine 3':5' Cyclic Monophosphate. These derivatives of cAMP are preferred for their enhanced ability to enter the cell. Preferably the cAMP modulating agent is capable of stimulating the cAMP pathway in the cell. More preferably, the cAMP modulating agent is a cAMP agonist. An example of a cAMP modulating agent includes forskolin.

The method of the invention can be used to culture a variety of cells, a preferably neuronal cells, including, but not limited to, dopaminergic neuron cells, cholinergic neuronal cells and serotonergic cells. Examples of suitable precursor cells include mesencephalic cells, basal forebrain cells or spinal cord cells and nucleus raphe cells. The invention also provides a method for treating a neurological disorder, such as Parkinson's disease, a method of introducing a gene product into a brain of a patient, and an assay for neurologically active substances. Advantageously, the method of the invention allows direct transplantation of the cultured cells without the need for enzymatic digestion to remove the cultured cells from a culture dish matrix.

The invention also provides a cell culture which includes about 80% to about 95% neurons. The percentage of glial cells in the cell culture is about 1% to about 5%, more preferably about 2% to about 3%, most preferably about 2% to about 2.5% for astrocytes and about 0.5% to 2%, more preferably 1% to 1.5%, and most preferably about 1% to 1.1% for oligodendrocytes. In contrast, no published work as of yet records percentages of neurons higher than 50%. Furthermore, the percentage of astrocytes in our culture system is extremely low as compared to any other known system.

DETAILED DESCRIPTION OF THE INVENTION

A first aspect of the invention provides a method for generating neuronal cells by proliferating and differentiating precursor cells. In the proliferating step, the number of precursor cells is increased. According to the invention, precursor cells are incubated in the presence of proliferating media which includes basic fibroblast growth factor (bFGF). More preferably the precursor cells are obtained from a human fetal tissue between embryonic week 5 to embryonic week 8. The proliferating step of the invention provides an expansion of precursor cells by more than 1000-fold and thus decreases the problem of obtaining sufficient cells for a reliable, effective clinical cell transplantation.

In the differentiating step, the precursor cells are induced to differentiate into neuronal cells. The differentiating step of the invention includes the step of incubating the precursor cells in a differentiation vessel in the presence of differentiating media in a manner effective to form a free-floating reaggregation of differentiated cells (e.g., an aggregation that is not adhered to a surface of the differentiation vessel). Formation of a free-floating reaggregate of differentiated cells in the differentiation step of the invention obviates the need for mechanical or enzymatic dissociation of the differentiated cells which generally causes disruption of axo-dendritic trees and cell loss. Additionally, the reaggregates of differentiated cells can be directly loaded into a stereotactic needle and transplanted in toto.

The differentiation media can include differentiating agents such as cyclic adenosine 3',5'-phosphate (cAMP), cAMP modulators, dopamine and ascorbic acid. Preferably cAMP is N6,2-O-dibutyrladenosine 3':5' cyclic monophosphate (dbcAMP) and/or 8-bromoadenosine 3':5' cyclic monophosphate. These derivatives of cAMP are preferred for their enhanced ability to enter the cell. Preferably the cAMP modulating agent is capable of stimulating the cAMP pathway in the cell. More preferably, the cAMP modulating agent is a cAMP agonist. An example of a cAMP modulating agent includes forskolin. As an alternative to dopamine, L-Dopa can be added as a differentiating agent. L-Dopa is converted in the cell into dopamine and released. Preferably ascorbic acid is L-ascorbic acid, although D-ascorbic acid can be used.

In a preferred embodiment, the differentiated cells are dopaminergic neurons. Dopaminergic neurons generated by the method of the invention are the first known dopaminergic neurons derived from in vitro expanded precursors that function in vivo. Dopaminergic neurons cultured using the method of the invention are particularly suitable for use in the treatment of Parkinson's disease.

I. Method of Culturing Cells

A first aspect of the invention provides a method for generating a differentiated cell culture by proliferating and differentiating a population of precursor cells. The method of the invention is applicable to a wide variety of precursor and differentiated cells. In a preferred embodiment, the method of the invention is used to generate differentiated neural cells.

A. Proliferating Step

In the proliferating step of the invention, precursor cells are incubated in proliferating media to increase the number of precursor cells. As used herein, the term "precursor cell" refers to a cell that is capable of differentiating to form a specific cell type, but does not yet express proteins associated with a specific cell type.

Typically, the precursor cells used in connection with the invention are cells that are associated with the central nervous system (CNS), referred to as CNS stem cells. The term "central nervous system" refers to the part of the nervous system of an animal that is the main site of integration of nervous activity. The central nervous system generally includes a brain or cerebral ganglia and a nerve cord. More preferably, the precursor cells are mammalian CNS stem cells, most preferably human fetal cells. CNS stem cells include cells from ventral midbrain, dorsal midbrain, lateral ganglionic eminence, hippocampus, cerebral cortex, striatum, septum, diencephalon, hindbrain and spinal cord. Preferably, the precursor cells are from the midbrain.

Most preferably, the method of the invention employs precursor cells obtained during a "sensitive period" before the cells have differentiated. As used herein, the "sensitive period" is the period during which precursor cells can be obtained that produce a very large number of a specific differentiated cell subtype. Preferably, the method of the invention employs precursor cells obtained from the midbrain before the cells differentiate into dopaminergic neurons. The inventors have found that later precursors under identical conditions produce much lower amounts of dopaminergic neurons in vitro. The sensitive period is the rat embryonic day 10 to embryonic day 12. In human fetal tissue the sensitive age is between embryonic week 5 to embryonic week 8.

According to the invention, precursor cells are triturated as described by Studer, L. in Current Protocols in Neuroscience (eds McKay, R. D. & Gerfen, C. R.) John Wiley & Sons Inc., New York, 1997) and dispersed in calcium/magnesium free HBSS (Hank's balanced salt solution) to a quasi single cell suspension. As used herein, the term "quasi single cell suspension" means that at least 80% of the cells are present as single cells and the remaining cells form small clusters of less than 200 cells. Preferably the suspension has a concentration of about $50 \times 10^3$ cells/ml to about $500 \times 10^3$ cells/ml, more preferably about $100 \times 10^3$ cells/ml to about $250 \times 10^3$ cells/ml, most preferably about $150 \times 10^3$ cells/ml to about $200 \times 10^3$ cells/ml.

The suspension of precursor cells is then plated onto proliferating medium. As used herein, the term "proliferating medium" refers to a solid or liquid substrate that can support cell growth. Typically, proliferating medium provides water, a source of energy, carbon, nitrogen, mineral elements, and vitamins. The medium may consist of pure compounds (defined medium) or crude animal or plant extracts (complex medium). The term "defined medium" refers to the fact that all the components and their concentrations are known. Usually the term is used in contrast to "serum-containing" medium where not all the components and their concentrations are known. The medium is preferably a solution of nutrients, water, salts, sugars, amino acids etc. containing the source of energy for the cells and also containing some hormones (e.g. progesterone) and trace elements (e.g. selenite) that enhance their general growth and survival. More preferably, the proliferating media includes serum free medium. Examples of serum free media include Dulbecco's Modified Eagle's Medium (DMEM) and Neurobasal® medium. Preferably, the proliferating media includes supplements such as $N_2$ supplement and/or B27 supplement. More preferably, the proliferating media is coated a substance that makes the surface of the petri dish sticky and facilitates attachment of the stem cells. Preferably, the surface is coated with polyornithine and fibronectin before the cells are plated. Polyomithine and fibronectin are preferred for use in the method of the invention because they facilitate adherence of the cells to the medium but still allow the cells to proliferate because they do not cause cell differentiation (in contrast to other substrates used in cell culture, such as laminin).

According to the invention, the proliferating medium is supplemented with basic fibroblast growth factor (bFGF). Preferably the medium is supplemented with bFGF on a daily basis, for example, by adding a solution containing bFGF dissolved in buffer. An example of a suitable buffer is phosphate buffered saline (PBS) and bovine serum albumin. A preferred bFGF solution contains about 5 µg/ml to about 20 µg/ml bFGF, more preferably about 7 µg/ml to about 15 µg/ml bFGF, most preferably about 10 µg/ml to about 10.5 µg/ml bFGF. Preferably the bFGF solution contains about 0.05% to about 0.5%, more preferably about 0.1% to about 0.2% bovine serum albumin.

About 1 µl to about 20 µl, more preferably about 5 µl to about 10 µl of the bFGF solution is added to a cell culture containing about 5 ml medium to produce a final concentration of about 5 ng/ml to about 100 ng/ml bFGF (final concentration in the medium), more preferably about 10 to about 20 ng/ml (final concentration in the medium).

The precursor cells are incubated for about 5 to about 10 days, more preferably about 5 to about 7 days. Although expansion beyond the first week in culture leads to an exponential increase in cell number, the percentage of dopamine neurons obtained from long term expanded precursors decreases rapidly, corresponding to only about 1–2% of the total population.

Additional factors that promote proliferation of precursor cells include fibroblast growth factor 4 (FGF4) and vasointestinal peptide (VIP).

B. Differentiating Step

In the differentiating step, the precursor cells are transformed into differentiated cells. As used herein, a "differentiated cell" is a cell that produces specialized proteins associated with a specific cell type. The method is applicable to a variety of cell types. However, the method is preferably used to culture differentiated neural cells. As used herein, the term "neuronal cells" refers to neurons. In contrast, the term "neural cells" refers more broadly to cells associated with the central nervous system (CNS) of an organism, for example, neurons, glial cells, precursor cells, etc. For example, the method of the invention can be used to generate differentiated neuronal cells such as dopaminergic, cholinergic or serotonergic neuronal cells from precursor cells from the midbrain/hindbrain junction, the basal forebrain and spinal cord or nucleus raphe, respectively. The invention is most preferably directed towards a method of proliferating and differentiating mesencephalon precursor cells to form functional dopaminergic neurons.

As used herein, the term dopaminergic neuronal cells refers to those cells generally found in the region of the ventral midbrain (VM) known as the substantia nigra pars compacta that project to the striatum. The precursor cells are typically found near the midbrain/hindbrain junction of an intact brain. Dopaminergic neurons can be characterized by their secretion of dopamine as a neurotransmitter and high levels of expression of tyrosine hydroxylase (TH), an enzyme that catalyzes the rate limiting step in the biosynthesis of dopamine.

In the differentating step of the invention, precursor cells are combined with differentiation medium in an incubation vessel and incubated for an amount of time sufficient to allow for the differentiation of the precursor cells into neuronal cells. Neurobasal/B27 medium (Gibco, Life Technologies) with or without serum supplement (1–10% fetal bovine serum) is a preferred differentiation medium. Like proliferation medium, differentiation medium contains a variety of nutrients necessary for cell survival. However, in contrast to proliferation medium, differentiation medium does not include mitogens which enhance cellular proliferation, for example bFGF. Additionally, differentiation medium may contain supplements to enhance differentiation, such as B27. Those of skill in the art are familiar with a variety of media suitable for use as differentiation media. The yield of differentiated cells after expansion and differentiation is typically about 15% to about 20%.

1. Reaggregation System

According to the invention, a reaggregation system is used in the differentiating step. In contrast to conventional cell cultures in which cultured cells are adhered to a surface of incubation vessel, the reaggregation system of the invention is a three-dimensional system that allows conversion of precursor cells into differentiated cells which exist in the differentiating media as free-floating reaggregates. As used herein, the phrase "adhered to" refers to cellular attachment via receptors on the cell surface, such as the interaction between cells and a cell culture matrix containing laminin, fibronectin, polylysine or other attachment factors. Advantageously, the cells cultured according to the reaggregation system of the invention can be transplanted without enzymatic digestion to remove the cells from the culture dish matrix. Enzymatic digestion tends to kill most cultured cells.

In the reaggregation system of the invention, the incubation vessel is rotated during incubation in a manner effective to form a differentiated cell cluster that is not adhered to any of the surfaces of the incubation vessel. Examples of suitable incubation vessels include enclosed spheres, tubes or drums. Generally, suitable incubation vessels are polystyrene based plastic tubes, for example, Falcon #2095. The quality of the tubes is important as cells might adhere to other plastics despite the rotational movement. Additionally, other plastics might negatively influence cell survival during differentiation. Most preferably, the incubation vessel is a roller tube or drum such as the roller drum available from Bellco Glass, Inc. (product number 7736-10164). According to the invention, the incubation vessel is slowly rotated around a horizontal axis during incubation to prevent attachment of single cells to the incubation vessel and to further interaction among cells to enhance aggregation. Preferably, the incubation vessel revolves at a speed of about 1 to about 4 rotations per minute. Most preferably, the incubation vessel is placed in a tissue culture incubator and tilted 5 degrees.

According to the invention, the precursor cells are incubated in the differentiation medium for about 5 to about 10 days, more preferably about 5 to about 7 days.

2. Differentiation Factors

According to another aspect of the invention, the differentiation medium includes at least one differentiation factor which improves differentiation of precursor cells into differentiated cells. Differentiation factors of the invention include cyclic adenosine 3',5'-phosphate (cAMP), cAMP modulators, dopamine and ascorbic acid. As used herein, cAMP includes N6,2-O-dibutyrladenosine 3':5' cyclic monophosphate (dbcAMP) and/or 8-bromoadenosine 3':5' cyclic monophosphate. These derivatives of cAMP are preferred for their enhanced ability to enter the cell.

As used herein, the term cAMP modulator refers to a molecule that is capable of up-regulating or stimulating cAMP production within a cell. Preferably, the cAMP modulating agent is a cAMP agonist. The cAMP modulator can be exogenous to the patient's system or may be an endogenous compound. For example, the cAMP modulator can be a naturally occurring peptide, protein or enzyme, or a peptide or protein fragment which catalyzes the production of cAMP. An examples of a suitable cAMP modulator is forskolin.

As an alternative to dopamine, the differentiating agent can includes substances which stimulate dopamine production or are converted into dopamine in vivo ("dopamine simulator"). For example, L-Dopa can be added as a differentiating agent. L-Dopa is converted in the cell into dopamine and released. Ascorbic acid includes L-ascorbic acid and D-ascorbic acid, although L-ascorbic acid is preferred.

Preferably, the differentiated media includes at least one of cAMP, forskolin, dopamine and ascorbic acid. Preferably, cAMP is present in a concentration from about 1 $\mu$M to about 5 mM, more preferably about 10 $\mu$M to about 1 Mm. Typically, differentiation media containing cAMP results in about a 50% to about 300% increase in the total number of differentiated neural cells from precursor cells. Most typically, an increase in tyrosine hydroxylase immunoreactive (TH-ir) cells, also called dopaminergic cells is observed. Preferably forskolin is present in the differentiation medium at a concentration from about 1 $\mu$M to about 100 $\mu$M, more preferably about 2 $\mu$M to about 10 $\mu$M. Typically, differentiation media containing forskolin results in about a 40% to about 150% increase in the total number of differentiated neural cells, particularly TH-ir cells. Preferably dopamine is present at a concentration from about 0.1 $\mu$M to about 1 mM, more preferably about 1 $\mu$M to about 1 mM to provide about a 300% to about 700% increase in the total number of TH-ir cells. The effects of cAMP, forskolin and dopamine appear to be additive.

Addition of ascorbic acid to a cell culture during differentiation dramatically increases the percentage of resulting functional neuronal cells, particularly TH-ir cells. Preferably ascorbic acid is included in connection with dopamine to prevent auto-oxidation of dopamine in the medium (the effects of dopamine and ascorbic acid are additive). Although, ascorbic acid by itself has a stronger effect than dopamine on induction of dopaminergic neurons. Typically an average about 5 to about 20 fold (500 to 2000%) increase in TH-ir neurons is observed. This surprising effect of ascorbic acid is not observed with other antioxydative agent. Without intending to be bound by theory, it is believed that ascorbic acid acts via a mechanism distinct from its antioxydative properties. Because ascorbic acid is also an essential nutritional supplement (Vitamin C), it is unlikely to have unwanted side effects.

II. Differentiated Cell Culture

The invention also provides a differentiated cell culture which includes neural cells that function in vivo. Preferably, the differentiated cell culture includes dopaminergic neurons that function in vivo. As used herein, the phrase "function in vivo" means that the cells can survive in a relevant animal model, retain their identity after transplantation, integrate into the host brain, and improve animal behavior.

The invention also provides a cell culture which includes about 80% to about 95% neurons. The percentage of glial cells in the cell culture is about 1% to about 5%, more preferably about 2% to about 3%, most preferably about 2% to about 2.5% for astrocytes and about 0.5% to about 2%, more preferably 1% to 1.5%, and most preferably about 1% to 1.1% for oligodendrocytes. In contrast, no published work as of yet records percentages of neurons higher than 50%. Furthermore, the percentage of astrocytes in our culture system is extremely low as compared to any other known system.

III. Methods of Use

A. Treatment of Neurological Disorders

In one embodiment, the present invention provides a method of treating a patient suffering from a neurological disorder, such as a central nervous system disorder, or alleviating the symptoms of such a disorder, by administering cells cultured according to the method of the invention to the patient's brain. As used herein, the terms "treating" and "treatment" refer to curative therapy, prophylactic therapy, and preventative therapy. The term "therapy" as used herein, refers to therapeutic methods for reducing or eliminating the symptoms of the particular disorder for which treatment is sought. The term "patient" as used herein generally refers to any warm blooded mammal, such as humans, non-human primates, rodents and the like which is to be the recipient of the particular treatment. Examples of neurological disorders include Parkinson's disease, Huntington's disease, Alzheimer's disease, severe seizure disorders including epilepsy, familial dysautonomia as well as injury or trauma to the nervous system, such as neurotoxic injury or disorders of mood and behavior such as addiction and schizophrenia.

In this method of the invention, precursor cells are cultured in vitro as described above to form differentiated neuronal cells which are then transplanted into the brain of a patient in need thereof.

1. Formulations

After the cell reaggregate is formed according to the cell culturing method previously described, the reaggregate is suspended in a physiologically compatible carrier. As used herein, the term "physiologically compatible carrier" refers to a carrier that is compatible with the other ingredients of the formulation and not deleterious to the recipient thereof. Those of skill in the art are familiar with physiologically compatible carriers. Examples of suitable carriers include cell culture medium (e.g., Eagle's minimal essential media), phosphate buffered saline, and Hank's balanced salt solution+/−glucose (HBSS).

The volume of cell suspension administered to a patient will vary depending on the site of implantation, treatment goal and amount of cells in solution. Typically the amount of cells administered to a patient will be a "therapeutically effective amount." As used herein, a therapeutically effective amount refers to the number of transplanted cells which are required to effect treatment of the particular disorder. For example, where the treatment is for Parkinson's disease, transplantation of a therapeutically effective amount of cells will typically produce a reduction in the amount and/or severity of the symptoms associated with that disorder, e.g., rigidity, akinesia and gait disorder.

It is estimated that a severe Parkinson's patient will need at least about 100,000 surviving dopamine cells per grafted side to have a substantial beneficial effect from the transplantation. As cell survival is low in brain tissue transplantation in general (5–10%) an estimated 1–4 million dopaminergic neurons should be transplanted. The invention delivers aggregates with about 15% TH cells and containing about 50,000–100,000 cells in total (7500–15000 TH cells/ aggregate). This means that for a successful therapy about 100–500 aggregates should be transplanted per patient side. The aggregates are collected together and then loaded directly into a stereotactic needle. Aggregates do not need any special formulation if total duration of the implantation procedure is less than 1 hour. Preferentially, the prepared spheres are maintained in medium and will be loaded into the needle immediately before introducing the needle into the patients brain.

2. Methods of Administration

According to the invention, the cell reaggregate is administered to the patient's brain. The reaggregate may be implanted within the parenchyma of the brain, in the space containing cerebrospinal fluids, such as the sub-arachnoid space or ventricles, or extraneurally. As used herein, the term "extraneurally" is intended to indicate regions of the patient which are not within the central nervous system or peripheral nervous system, such as the celiac ganglion or sciatic nerve. "Central nervous system" is meant to include all structures within the dura mater.

Typically, the reaggregations are administered by injection into the brain of the patient. Injections can generally be made with a sterilized syringe having an 18–21 gauge needle. Although the exact size needle will depend on the species being treated, the needle should not be bigger than 1 mm diameter in any species. Those of skill in the art are familiar with techniques for administering cells to the brain of a patient.

3. Diseases a. Parkinson's disease

Parkinson's disease (PD) is characterized by the progressive loss in function of dopaminergic neurons. The progressive loss of dopaminergic function interferes with the normal working of the neuronal circuitry necessary for motor control so that patients with PD show characteristic motor disturbances such as akinesia, rigidity and rest tremor. Other symptoms include pain, impaired olfaction, alterations of personality and depression. Quinn et al., (1997) *Baillieres Clin. Neurol.* 6:1–13.

According to the invention, dopaminergic neuronal cells are generated using the cell culturing method described above. The dopaminergic cells are then administered to the brain of the patient in need thereof to produce dopamine and restore behavioral deficits in the patient. Preferably, the cells are administered to the basal ganglia of the patient.

b. Alzheimer's disease

Alzheimer's disease involves a deficit in cholinergic cells in the nucleus basalis. Thus, a subject having Alzheimer's disease may be treated by administering cells cultured according to the method of the invention that are capable of producing acetylcholine.

c. Huntington's disease

Huntington's disease involves a gross wasting of the head of the caudate nucleus and putamen, usually accompanied by moderate disease of the gyrus. A subject suffering from Huntington's disease can be treated by implanting cells cultured according to the method of the invention that are capable of producing the neurotransmitters gamma amino butyric acid (GABA), acetylcholine, or a mixture thereof.

4. Gene Therapy

In an additional embodiment of the invention, the cultured cells may be transfected with a nucleic acid which encodes a neurologically relevant polypeptide. The term "neurologically relevant peptide" generally refers to a peptide or protein which catalyzes a reaction within the tissues of the central nervous system. Such peptides may be naturally occurring neural peptides, proteins or enzymes, or may be peptide or protein fragments which have therapeutic activity within the central nervous system.

According to this aspect of the invention, precursor cells are cultured in vitro as described above and an exogenous gene encoding a desired gene product is introduced into the cells, for example, by transfection. The transfected cultured cells can then be administered to a patient with a neurological disorder.

a. Genes of interest

Examples of neurologically relevant peptides include neural growth factors and enzymes used to catalyze the production of important neurochemicals or their intermediates. The peptide encoded by the nucleic acid may exogenous to the host or endogenous. For example, an endogenous gene that supplements or replaces deficient production of a peptide by the tissue of the host wherein such deficiency is a cause of the symptoms of a particular disorder. In this case, the cell lines act as an artificial source of the peptide. Alternatively, the peptide may be an enzyme which catalyzes the production of a therapeutic or neurologically relevant compound. Again, such compounds may be exogenous to the patient's system or may be an endogenous compound whose synthetic pathway is otherwise impaired. Examples of neurologically relevant compounds include tyrosine hydroxylase, nerve growth factor (NGF), brain derived neurotrophic factor (BDGF), basic fibroblast growth factor (bFGF) and glial cell line derived growth factor (GDGF).

b. Gene constructs

Typically the gene of interest is cloned into an expression vector. As used herein, the term "expression vector" refers to a vector which (due to the presence of appropriate transcriptional and/or translational control sequences) is capable of expressing a DNA molecule which has been cloned into the vector and of thereby producing a polypeptide or protein. A nucleic acid molecule, such as DNA, is said to be "capable of expressing" a polypeptide if it contains nucleotide sequences which contain transcriptional and translational regulatory information and such sequences are "operably linked" to a nucleotide sequence that encodes the polypeptide. An operable linkage is a linkage in which the regulatory DNA sequences and the DNA sequence sought to be expressed are connected in such a way as to permit gene expression. Regulatory elements include elements such as a promoter, an initiation codon, a stop codon and a polyadenylation signal.

Expression of the cloned sequences occurs when the expression vector is introduced into an appropriate host cell. In this case, the preferred host cell is a neuronal cell. Procedures for preparing expression vectors are known to those of skill in the art and can be found in Sambrook et al., *Molecular Cloning: A Laboratory Manual*, 2nd Ed. Cold Spring Harbor Press, Cold Spring Harbor, N.Y. (1989).

IV. Assay

Another aspect of the invention provides an assay for evaluating the effect of substances on differentiated cells, preferably differentiated neuronal cells. The assay can be used to discover drugs capable of regulating the survival, proliferation or genesis of neuronal cells. According to this aspect of the invention, a population of neuronal cells is produced by the cell culturing method described above. The population of cells is contacted with a substance of interest and the effect on the cell population is monitored. The impact on the cell population can be monitored, for example, by determining whether the substance causes an increase or decrease in the expression of a reporter gene by examining the level of its protein, RNA, biological activity or other methods. For example, in one immunocytochemical method, the dopaminergic cells are monitored to determine the impact of a substance on the expression of tyrosine hydroxylase.

Substances of interest include extracts from tissues or cells, conditioned media from primary cells or cell lines, polypeptides whether naturally occurring or recombinant, nucleotides (DNA or RNA) and non-protein molecules whether naturally occurring or chemically synthesized.

EXAMPLES

Example 1

Tissue Culture Expansion

Tissue was obtained from the ventral mesencephalon of E12 rat embryos (Sprague Dawley, plug day=day 0,) as described by Studer et al. in *Current Protocols in Neuroscience* (eds McKay, R. D. & Gerfen, C. R.) John Wiley & Sons Inc., New York, (1997).

Tissue pieces were spun in a centrifuge at 209 g for 5 minutes and mechanically triturated to a quasi single cell suspension in HBSS and counted. 5 ml of cell suspension at a concentration of 150–200×$10^3$ cells/ml was plated on a 10 cm culture dish containing DMEM/F12/N2 medium (Bottenstein, J. E. & Sato, G. H. Growth of a rat neuroblastoma cell line in serum-free supplemented medium. Proc. .Natl.Acad.Sci.USA 76, 514–517 (1979) (modified according to Johe, K. K., Hazel, T. G., Müller, T., Dugich-Djordjevic, M. M. & McKay, R. D. G. Single factors direct the differentiation of stem cells from the fetal and adult central nervous system. Genes and Development 10, 3129–3140 (1996)) that had been previously coated with polyornithine (15 ug/ml) and fibronectin (1 ug/ml).

bFGF was added to the culture medium on a daily basis to a final concentration of 10–20 ng bFGF/ml medium. The medium was changed every other day.

Figure 1:
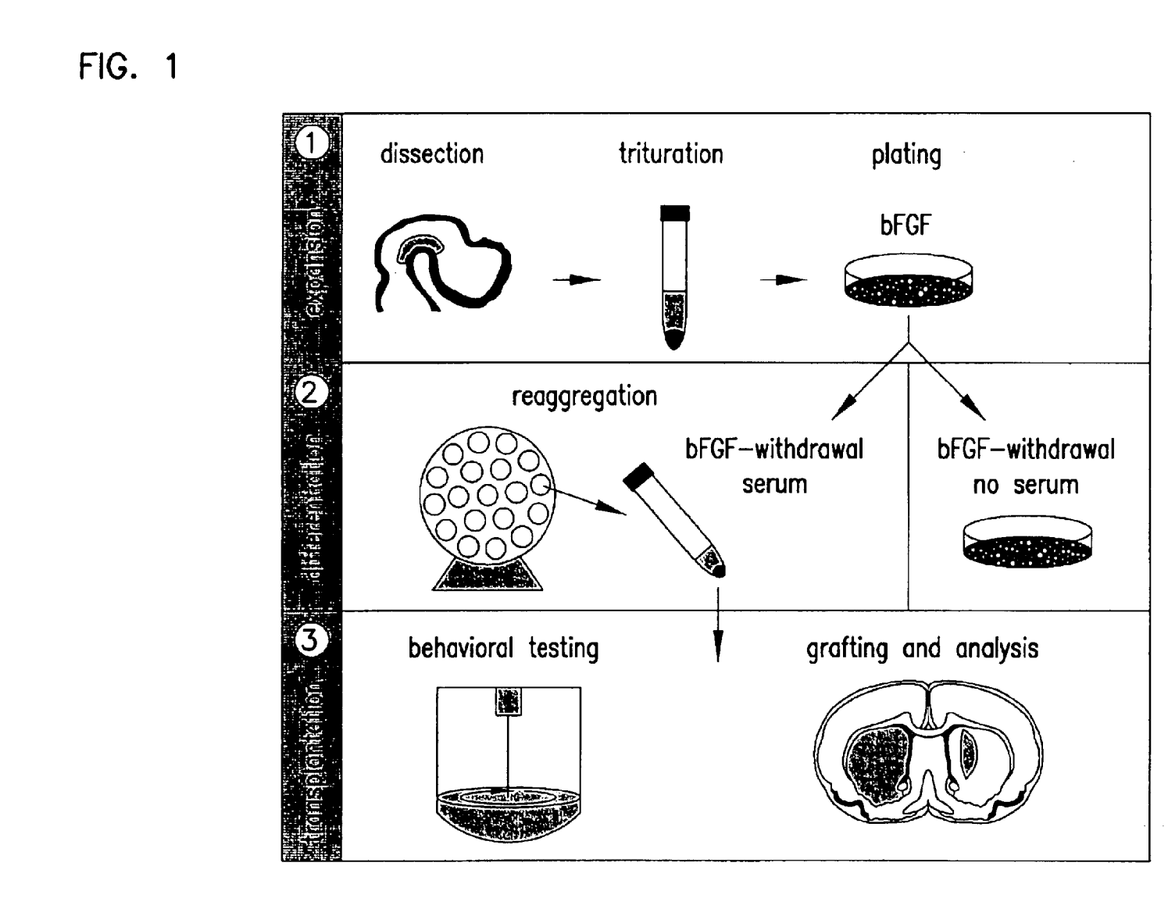
FIG. 1 is a schematic diagram of the cell culturing method of the invention.
Figure 2:
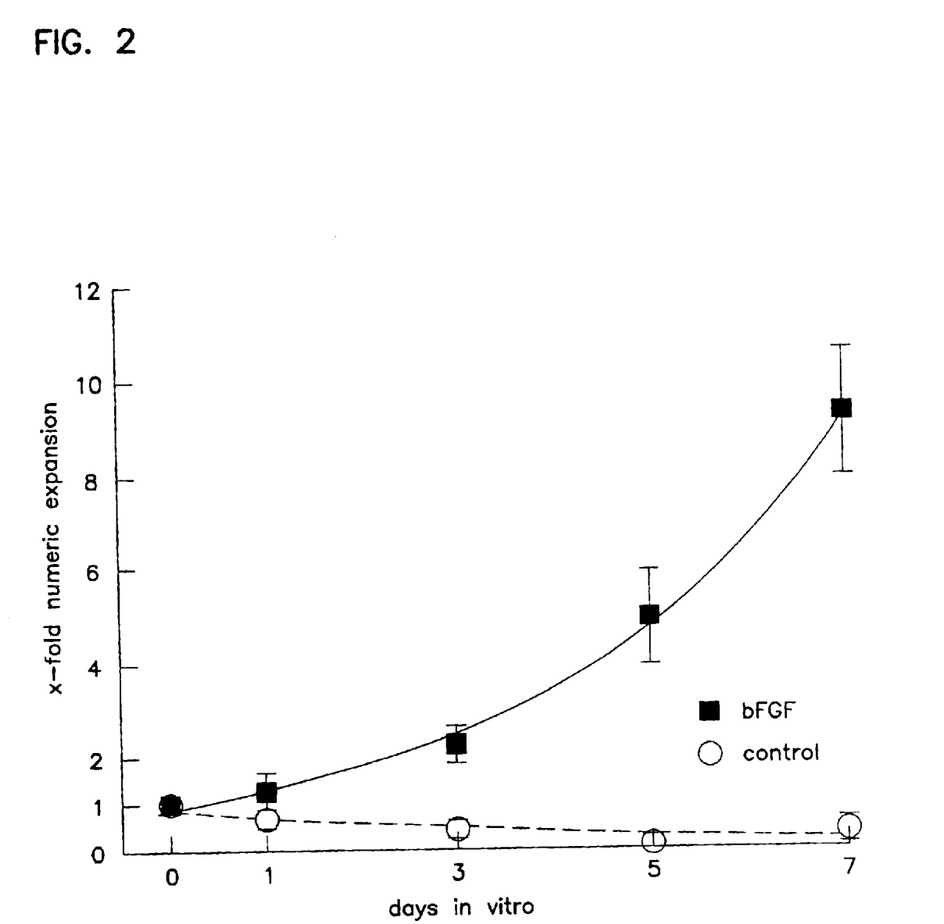
FIG. 2 is a graph showing the numeric expansion of cells cultured in the presence of basic fibroblast growth factor (bFGF).
Figure 3:
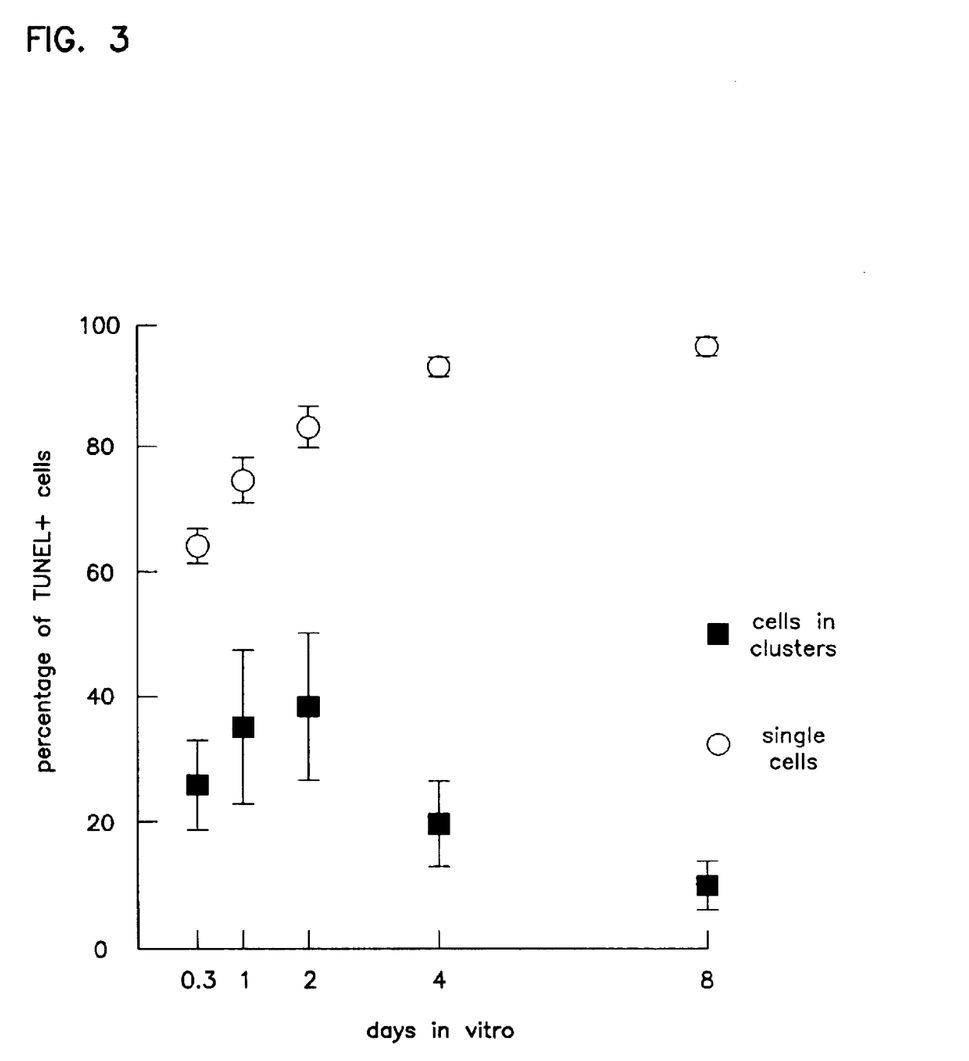
FIG. 3 is a graph showing the percentage of TUNEL for cells grown in clusters compared to single cells. The graph shows that all surviving cells are growing in clusters.

After 1 week of treatment with bFGF, the cells proliferated and formed clusters that grew to macroscopic size increasing the cell number from 800×$10^3$ to 7,417×$10^3$+/−1,066×$10^3$ cells (N=12). Cultures grown without bFGF exhibited a substantial net cell loss. FIG. 2 shows a comparison of the growth rate between bFGF treated cells and control cultures. Additionally, after treatment with bFGF all surviving cells were immunoreactive for the nestin intermediate filament a marker for immature neuroepithelial precursors. The procedure used to determine the immunoreactivity of the cells for the nestin intermediate filament marker can be found in Frederiksen et al., (1988) *J.Neurosci.* 8, 1144–1151 and Lendahl et al., (1990) *Cell* 60, 585–595. TH monoclonal 1:10000 (Sigma), nestin #130 polyclonal 1:500 (M. Marvin and R. D. G. McKay, NINDS, NIH, Bethesda, Md.).

A. bFGF Receptor Expression bFGF receptor expression was studied to determine the percentage of cells that respond to bFGF to determine what fraction of cells would be capable of expanding. bFGF-receptor expression was assayed by standard immunohistochemistry procedures using bFGF receptor monoclonal 1:100 (Sigma). bFGF receptor expression was present in most cells throughout expansion (88+/−4%).

B. Tunel

Terminal deoxynucleotidyl transferase-mediated deoxyuridine triphosphate nick end labeling (TUNEL; Boehringer-Mannheim) was performed according to the manufacturer's specifications. Briefly, cells, cultured as described above, were fixed in 4% paraformaldehyde/0.15% picric acid after 7 hours, 1 day, 2 days, 4 days or 8 days of expansion and labeled using a TUNEL cell death kit (Boehringer-Mannheim, 1684817).

Briefly, the TUNEL reaction labels DNA end fragment. The number of DNA end fragments is increased as a cell undergoes death due to DNA fragmentation. All negative controls (no deoxynucleotidyl transferase in the reaction mixture) were devoid of any labeling.

TUNEL labeling demonstrated that cells not responding to the mitogenic activity of bFGF, as assessed by time lapse photomicrography, were prone to cell death. This shows that cellular proliferation is stimulated by bFGF. The proliferating cells form clusters as assessed by time lapse photography. Cells that did not form clusters and did not divide in vitro were prone to cell death. In contrast, cell death within proliferating clusters was relatively rare. As clusters are derived from dividing cells, only proliferating cells (that respond to bFGF) survive. This leads to a near pure population of precursors over time (differentiated cells die).

Example 2

Differentiation of Tissue Culture Cells

Differentiation was induced by removal of bFGF from the medium. Upon removal of bFGF from the culture medium, extensive aborizations developed interconnecting large clusters of cell bodies. The cells were grown on culture dishes, proliferated with bFGF for 1 week and then maintained in the absence of bFGF in serum-free medium for 6 days. This "bFGF withdrawal" without any other differentiation agents works when cells have grown to high cell density and are adherent to a substrate. For reaggregates Neurobasal/B27+/− serum is preferable.

Tissue culture was prepared as described in Example 1. The growth medium of expanded precursors from 3 independent culture series was collected after 5–7 days of differentiation under serum-free conditions and immediately stabilized by adding 88 $\mu$l of 85% orthophosphoric acid and 4.4 mg of metabisulfite to each sample ml. Additional cultures of the same series were placed in 5 ml Hank's basic salt solution (HBSS) for 25 minutes at 37° C. either under basal conditions (HBSS only) or under stimulation with 56 mM KCl. 56 mM KCl was added to assay evoked release, i.e., dopamine release in response to depolarization by KCl (depolarization by KCl leads to release of synaptic vesicles in neurons). This provides a more specific test than release in HBSS where synaptic release is not directly tested.

A. Ki-67

Cell proliferation during the differentiation phase was monitored by an immunohistochemical test for the proliferation marker Ki-67 using Ki67 polyclonal 1:1000 (Novocastra) and the procedure described by the manufacturer. No substantial cell proliferation occurred during the differentiation phase. Only a small fraction (1.2%+/−0.9%, N=10) of the cells were mitotically active after 7 days of differentiation.

B. TuJ1

Using general immunohistochemical procedures known to those of skill in the art and TuJ1 monoclonal 1:500 (Berkley Antibody Company), the cell bodies and fiber bundles were examined for immunoreactivity for β-tubulin type III. Cell bodies and fiber bundles were strongly immunoreactive for β-Tubulin type III (TuJ1). β-tubulin is a marker for neuronal cells and is used to confirm neuronal identity and dendrite outgrowth.

C. TH-IR

Using general immunohistochemical procedures known to those of skill in the art, the immunoreactivity of the cells to TH was examined using TH polyclonal 1:500 (Pel Freeze). While no tyrosine hydroxylase (a rate limiting enzyme in the synthesis of dopamine) immunoreactive (TH-ir) cells could be detected in the tissue at the time of dissection, after 7 days of differentiation 18.4%+/−5.1% of the total cell population was immunoreactive for TH. TH-ir cells were also immunoreactive for dopamine, dopamine transporter (DAT) and for TuJ1. The percentage of TH-ir cells is non-expanded cultures, grown without bFGF was 5.6+/−1.3%.

One E12 embryo yielded 100–120,000 nigral cells at the day of dissection that were then expanded 10 fold, 18.4% of which stained positive for TH (180–220,000 TH-ir cells). When compared to the total number of dopaminergic neurons present in the adult rat (26–30,000) (Guyenet et al., (1981) *Brain Res.* 213, 291–305 and Rosenthal, (1998) *Neuron* 20, 169–172) the expansion procedure of the invention leads to an estimated 7 fold increase in TH-ir cell number.

D. HPLC-Dopamine

Dopamine staining was carried out on cultures using dopamine polyclonal 1:500 (Chemicon). The cultures were fixed in 5% glutaraldehyde and 1% metabisulfite in Tris buffer and then kept in metabisulfite containing solutions prior to incubation in the secondary antibody. Dopamine was extracted by aluminum adsorption as described by Studer et al. (1996) *Brain Res.Bull.* 41, 143–150. Separation of the injected samples (20 µl) was achieved by isocratic elution on a Hewlett Packard Series 1050 HPLC system with a reverse-phase C18 column (3 µm particle size. 80×4.6 mm dimension, (ESA)) in a commercially available MD-TM mobile phase (ESA). The flow rate was set at 1 ml/min resulting in a working pressure of 100 bar and an elution time of 2.7 minutes for dopamine. The oxidative potential of the analytical cell (ESA Mod. 5011) was set at +325 mV. Results were validated by co-elution with dopamine standards under varying buffer conditions and detector settings. No dopamine was detected in unconditioned control medium and HBSS.

Reverse phase HPLC analysis with electrochemical detection demonstrated that 1 ml medium, collected from expanded precursors after 5–7 days of differentiation, contained between 80–250 pg of dopamine. Similar dopamine levels could be detected in the supernatant of differentiated cultures maintained in HBSS for 25 minutes (162+/−54 pg dopamine/ml HBSS, N=3).

Evoked release by exposing cultures to 56 mM KCl in HBSS for 25 minutes led to a 3–4 fold increase in dopamine levels in the supernatant (572+/−145 pg dopamine/ml, N=3). These data demonstrate that dividing precursor populations efficiently generate dopaminergic neurons.

Thus a more than 3 fold increase in the percentage of dopaminergic neurons (18.4%) derived from expanded and differentiated precursors was observed as compared to non-expanded and differentiated precursors (5.6%). When this is multiplied by a 10 fold increase in total cell number obtained during the expansion phase, an estimated 30 fold increase in the in vitro yield of nigral dopaminergic neurons is obtained.

E. BrdU

Bromodeoxy-Uridine (BrdU; 1 µM, Boehringer-Mannheim) was added to the serum-free medium at days 1,3 and 5 of the expansion phase. Cells were marked after plating with a 3 mm circle (Nikon) on the bottom of the plate (Johe et al., (1996) *Genes and Development* 10, 3129–3140). Cells were followed daily under phase contrast microscopy and pictures were taken from selected cells and cell clusters daily.

BrdU immunohistochemistry was performed after post-fixation in 95% Ethanol/5% glacial acetic acid and incubation in primary antibodies and nucleases (Amersham Life Science). An average of 41%+/−14% (N=12) of all dopaminergic cells had clearly incorporated BrdU. The percentage of BrdU labeling in the total cell population was 47%+/−21% (N=12). This is a minimum estimate as higher BrdU concentrations (10 µM) led to increased labeling rates but dramatically reduced overall cell viability (data not shown).

Bromodeoxy-Uridine (BrdU) labeling confirmed that differentiated dopaminergic neurons were derived from precursor cells that had proliferated in vitro.

F. TH-BrdU Double Immunohistochemistry

The cultures were analyzed by confocal microscopy with z-axis sectioning for TH-BrdU double labeling after differentiation. Appropriate FITC and LRSC labeled secondary antibodies were used for double immunohistochemistry TH-BrdU.

Example 3

Ascorbic Acid

Ascorbic acid was obtained from SIGMA (A-1417: Lot 105H0138) and used at various concentrations ranging from 1 nM–1 mM to obtain a dose-response curve. The effect of ascorbic acid on dopaminergic differentiation of long-term expanded mesencephalic precursors was tested during early and late proliferation as well as during cell differentiation.

A. Cell Culture and Immunohistochemistry

Briefly, E12 mesencephalic precursors were proliferated for 12–14 days in vitro with 20 ng/ml bFGF (average expansion factor 40–200 fold) followed by 4–7 days of differentiation upon bFGF withdrawal and exposure to the various differentiation agents refers to the experimental assay in general. We tested the effects of many possible differentiation agents such as NGF, BDNF, NT3, NT4/5, GDNF, SHH, FGF8, interleukin1, Neurturin, cGMP and many others. Ascorbic acid was found to be the most effective agent of all agents tested (see above) with respect to the yield of dopaminergic neurons that can be obtained from expanded precursors. The conclusion is that Ascorbic acid at 100 uM has an unsurpassed effect on dopaminergic differentiation in our expansion system.

Cells were treated with 100 uM ascorbic acid. Ascorbic acid was dissolved in PBS with 0.1% bovine serum albumin at 100 mM stock solution. It was then used in 1:1000 dilution by adding it directly into the culture medium Cells were then fixed in 0.15% picric acid/4% paraformaldehyde and stained for tyrosine-hydroxylase (PelFreeze P40101-0). The number of TH-ir cells per well were scored using a stereological counting frame.

Figure 5:
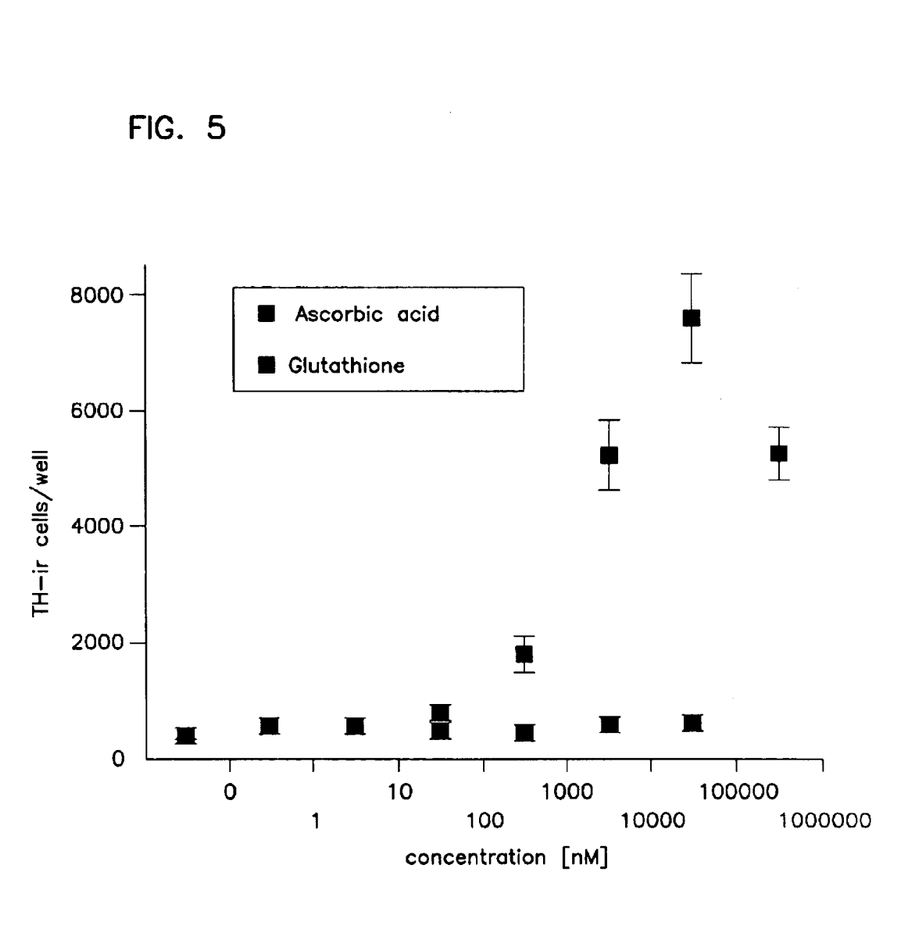
FIG. 5 is a graph showing the effect of ascorbic acid and glutathione on the number of TH-ir cells grown in a cell culture.

During cell differentiation ascorbic acid showed a strong dose-response relationship with a maximal effect at 100 µM (FIG. 5). Ascorbic acid has a very strong effect on dopaminergic differentiation at the time when differentiation is induced. This effect confirms the hypothesis that ascorbic acid is important at the step from the precursor to the differentiated neuron and increases the yield of neurons of the dopaminergic type.

B. Phase of Ascorbic Acid Activity

Figure 6:
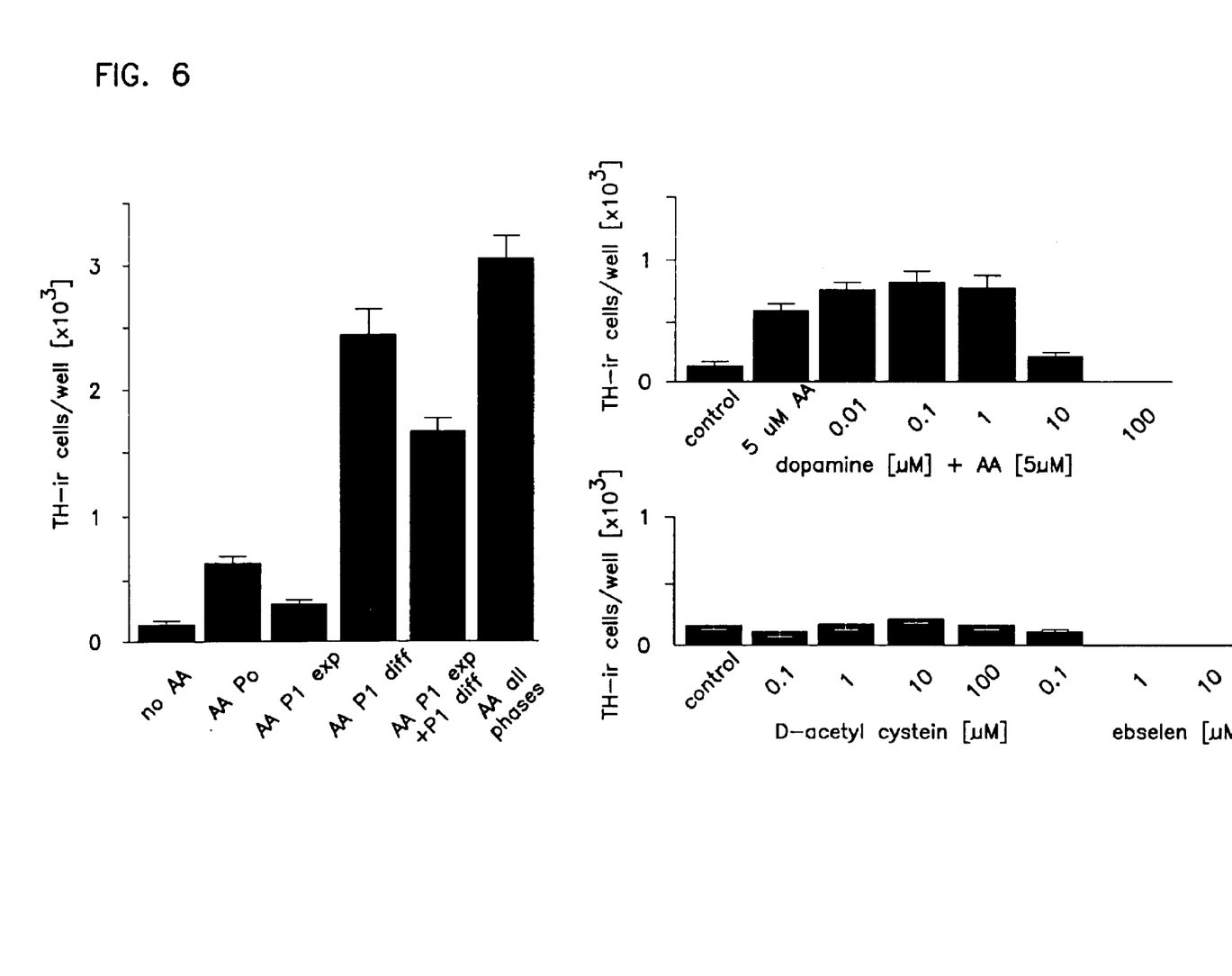
FIG. 6 is graphs showing the effects of ascorbic acid (AA), dopamine, and D-acetyl cysteine on the number of TH-ir cells grown in a cell culture.

To determine the phases during which ascorbic acid is most effective in our precursor system we treated the cells either during early expansion (Po exp.), late expansion (P1 exp.) or during cell differentiation (P1 diff.) as well as all the possible combinations (see FIG. 6). The results revealed that ascorbic acid acts mostly during the differentiation phase. Treatment during the late expansion phase has a slightly negative effect and treatment during the early expansion phase give a small improvement in dopaminergic yield.

C. Other Antioxidants

In addition to glutathione (FIG. 5) we also tested D-acetylcystein, ebselin and combinations thereof, for possible effects on dopaminergic differentiation. However, none of the antioxidants tested influenced dopaminergic cell number (FIG. 6). We also assessed the level of oxydative stress in our culture system by various assays.

Lipid peroxydation is a colorimetric assay (OXIS BIOX-YTECH® LPO-568™; Oxis International Inc.) and was used according to the specifications of the manufacturer. $H_2O_2$ assay measures the conversion of 2',7' dicholorofluorescin diacetate (Molecular Probes d-399) into 2',7' dicholorofluorescin catalyzed by $H_2O_2$. The assay was performed according to the specifications of the manufacturer. Immunohistochemistry for oxidative stress markers by the DAB-peroxidase technique was performed on cells differentiated in the presence or absence of ascorbic acid, glutathione or D-acetyl-cysteine plus ebselin. The following antibodies were used:

| Epitope | Antibody Type | Catalogue No. | Company |
|---|---|---|---|
| Anti-hemoxygenase I | monoclonal AB | OSA-111 | Stressgen |
| Anti-8-hydroxyguanosine | monoclonal AB | 12501 | QED Bioscience Inc. |
| Anti-Nitrotyrosine | polyclonal (sheep) AB | 24312 | Oxis International Inc. |

All these assays showed very low to undetectable levels of oxydative stress in our culture system in general. No significant differences between control, ascorbic acid and the other antioxidants tested were found regarding lipid peroxydation, $H_2O_2$ levels and staining intensity for oxydative stress markers (data not shown).

A dose response curve of the effect of stereoisomer D-iso-ascorbic acid was established using D-iso Ascorbic acid (I-0502 SIGMA). D-iso-ascorbic acid was used with the same protocol as L-ascorbic acid regarding stock solution, concentrations and mode of application. D-iso ascorbic acid has the same anti-oxydative properties but different other biological properties than ascorbic acid. Interestingly, the effect of D-iso-ascorbic acid a stereoisomer of ascorbic acid that has the same antioxydative properties but differs in the non-oxydative biological effects showed a much-decreased effectiveness. At optimum concentration of 100 μM the number of dopaminergic neurons obtained in the D-iso ascorbic acid group was 48% lower than in the ascorbic acid group.

D. In vitro Test of Dopaminergic Neurons Generated in the Presence of Ascorbic Acid To test the biochemical function of precursor derived tyrosine hydroxylase expressing (TH+) neurons, the supernatant was tested for dopamine release using reverse phase HPLC with electrochemical detection. Dopamine levels were assessed in conditioned medium (24 hours of incubation), HBSS buffer (15 minutes), HBSS buffer +56 mM KCl. Dopamine was subsequently extracted by aluminum absorption and measured by reverse phase HPLC with electrochemical detection.

Figure 7:
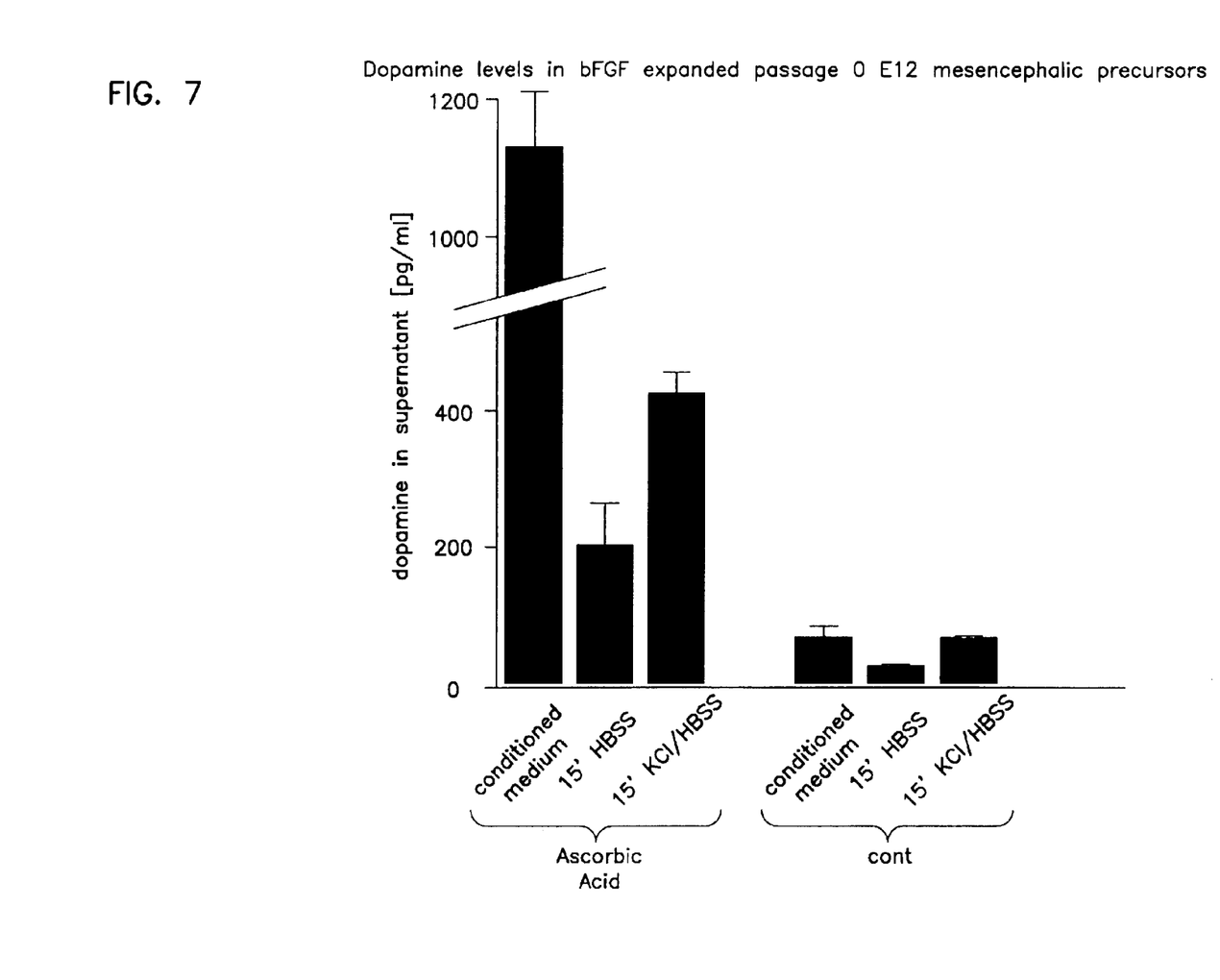
FIG. 7 is a graph showing dopamine levels in bFGF expanded precursor cells.
Figure 8:
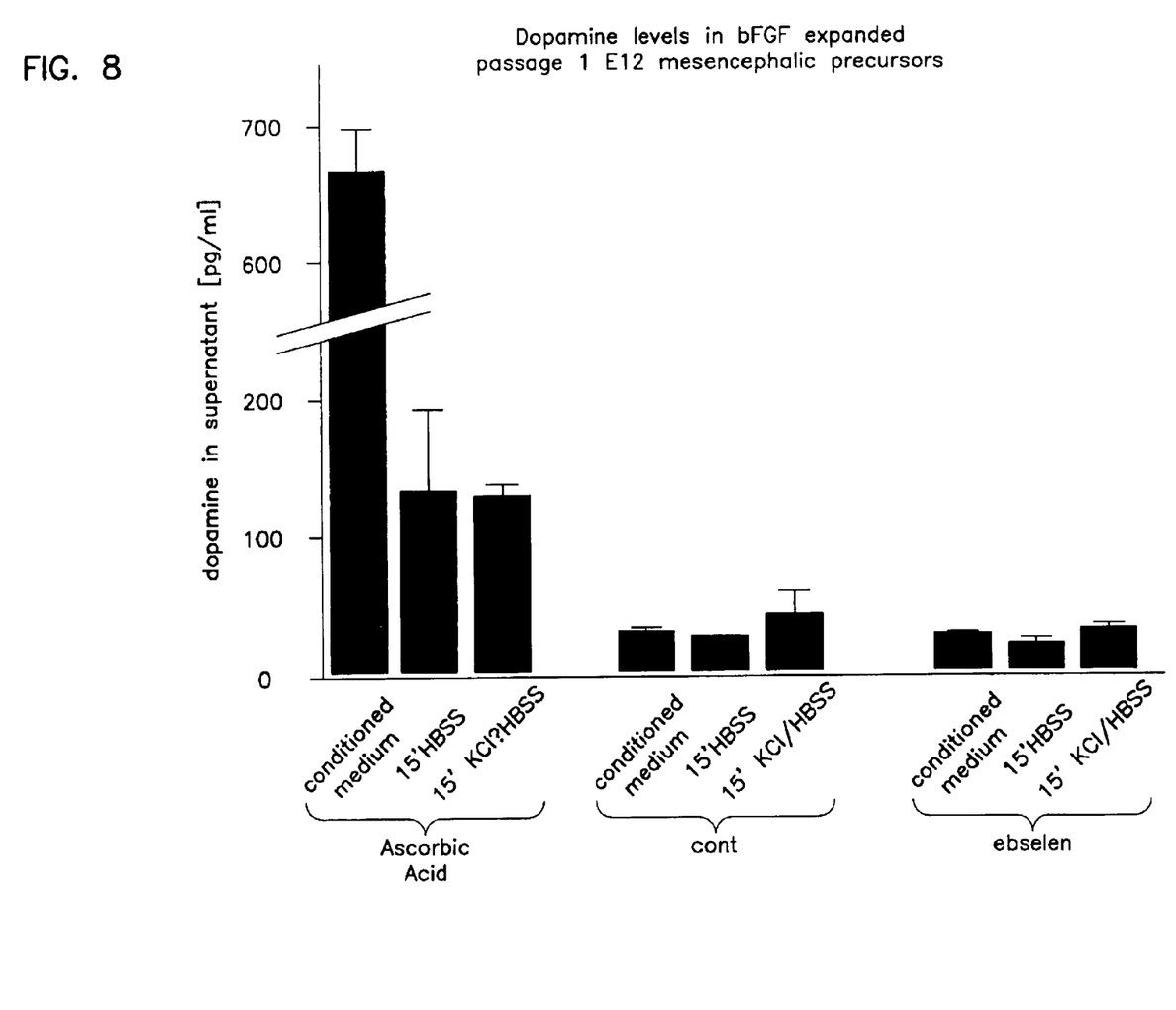
FIG. 8 is a graph showing dopamine levels in bFGF expanded precursor cells.

Conditioned medium, buffer solution and buffer solution supplemented with 56 mM KCl all showed a significant increase in dopamine levels after ascorbic acid treatment in short term expanded precursors (5–50 fold; Po) and in long-term expanded precursors (50–500 fold; P1) (see FIGS. 7 and 8)

E. Combination Treatment with cAMP, Ascorbic Acid and Dopamine

Combination treatment experiments were carried out with mesencephalic precursors expanded with bFGF for 11 days and differentiated in DMEM/F12/N2 medium in the presence or absence of ascorbic acid (100 uM), dopamine (1 nM–1 mM) and cAMP (1 mM). The data revealed that dopamine has only a very minor additional effect on the yield of dopaminergic neurons as compared to ascorbic acid treatment alone (see FIG. 6). cAMP and ascorbic acid have an additive effect on the yield of dopaminergic neurons from expanded precursors. Combination treatment of ascorbic acid and dopamine and of ascorbic acid and cAMP showed that dopamine contributes no significant additional effect to ascorbic acid treatment. The effects of ascorbic acid and cAMP appear additive.

Example 4

Reggregation System for Cellular Differentiation

Transplantation of cells that are differentiated on culture dishes entails mechanical or enzymatic dissociation with subsequent disruption of axodendritic trees and cell loss. Therefore we developed a reaggregation system that allows conversion of previously expanded precursors into dopaminergic neurons in free-floating spheres. These reaggregates can be directly loaded into a stereotactic needle and transplanted in toto.

A. Cell Culture

Cells were cultured as described in Example 1 and differentiated as free floating aggregates in a medium containing 10% fetal bovine serum (FBS) and maintained in a roller drum system. The cell suspension (200,000 cells/ml) was distributed in 15 ml Falcon tubes (1 ml/tube) and placed in a roller drum (Bellco) and rotated at a speed of 1–4 revolutions per minute and a temperature of 37° C. in a dry incubator (no additional humidity) in an atmosphere containing 5% CO2.

Medium in all these experiments described in this section was Neurobasal/B27 as described above. We tested the effect of GDNF, BDNF, SHH in the presence and in the absence of 10% fetal bovine serum (always with Neurobasal/B27 medium as a "basal medium")

After 7 days, the test tubes were removed from the roller drum and the reaggregation of the cells was examined immunohistochemistry after sectioning the cells (see below). Differentiation in the roller drum typically resulted in the formation of one large (0.6–1.2 mm in diameter) sphere/tube. Reaggregates were fixed in 4% paraformalehyde/0.15 picric acid in PBS for 30–60 minutes at room temperature, equilibrated in 30% sucrose, cut into 20 um thick sections on a freezing microtome and adhered to a gelatine precoated glass carrier according to standard histological guidelines.

The differentiation medium for reaggregate cultures consisted of Neurobasal®/2% B27® (Gibco, Life Technologies) with or without fetal bovine serum (FBS; 10%, Gibco), glial derived neurotrophic factor (GDNF; 10 ng/ml; Peprotech), brain derived neurotrophic factor (BDNF; 10 ng/ml; Peprotech), neurotrophin 4/5 (NT4/5; 10 ng/ml; Peprotech), SHH (2.5 μg/ml; kindly provided by Dr. Thomas Muller, at the Labrotory of Molecular Biology, currently at the Max Delbrueck Univ. in Berlin; SHH is now commercially avail. fro R&D).

B. Cell Phenotypes

Using standard immunohistochemical procedures known to those of skill in the art, the following antibodies were used to examine the neuronal phenotypes present in differentiated aggregates: GABA polyclonal 1:2000 (SIGMA), serotonin polyclonal 1:8000 (SIGMA), ChAT polyclonal 1:500 (Chemicon), GFAP polyclonal 1:100 (Chemicon), GalC monoclonal 1:50 (Boehringer-Mannheim), Neuronal phenotypes present in differentiated reaggregates were, in descending order of frequency, GABAergic (10–15%), serotonergic (3–5%) and cholinergic (<0.1%) neurons. The percentage of glial cells in differentiated reaggregates was low. In serum treated cultures 2.8%+/−1.2%, N=9 of the total cell population was immunoreactive for glial fibrillary acid protein (GFAP), an astrocytic marker. The percentage of astrocytes in non-serum treated cultures was even lower (1.1%+/−0.9%, N=9). No mature galactocerebroside (GalC)-ir oligodendrocytes could be detected in differentiated reaggregates under any of the conditions tested.

Supplementation of the differentiating medium with 10% fetal bovine serum (FBS) led to a dramatic increase of TH-immunoreactive (TH-ir) neurons in differentiated reaggregates with 6178+/−547 TH-ir neurons/sphere as compared to 1341+/−341 in cultures grown without FBS ($p<0.01$). The average volume of serum-treated reaggregates was 0.77+/−0.11 mm$^3$ resulting in a mean density of 10,749+/−2386 TH-ir cells/mm$^3$. The percentage of TH-ir cells was 14.1+/−4.2% in serum-treated reaggregates and 2.9+/−1.3% in the control group. (N=21 for the group treated with FBS; 11 for the control group).

Treatment with GDNF (10 ng/ml), BDNF (10 ng/ml), NT4/5 (10 ng/ml), or SHH (2.5 µg/ml) did not cause a significant increase in the total number of TH-ir cells/sphere in serum-supplemented medium (data not shown). However, under serum-free conditions, GDNF did significantly improve TH-ir cell yield as compared to control cultures (GDNF 3451+/−621, N=8; control group 1341+/−341, N=11; $p<0.05$). Because no growth factor could substantially exceed the effect of FBS, cultures produced for transplantation purposes were raised in 10% FBS without any additional growth factors.

Example 5

Transplantation of Tissue Culture Aggregates

A. Transplantation

Adult female Sprague Dawley rats (200–250 g) were lesioned by unilateral injection of 6-hydroxydopamine bromide at 2 sites along the MFB[44]. 6–7 reaggregates (corresponding to a total number of 3–4×10$^5$ cells) were loaded into a blunt 18 G spinal needle (Sherwood Medical) and deposited at the ipsilateral striatum of 6OHDA lesioned rats (AP +1.0 mm, ML −2.5 mm, and V −4.7 mm (coordinates relative to bregma), toothbar set at −2.5).

A. Behavior

Graft function was assessed as changes in amphetamine-induced rotation behavior. Automated assessment (Rota Count-8, Columbus Instruments) of amphetamine-induced rotational behavior (i.p injection of 5 mg d-amphetamine sulfate (SIGMA)/kg body weight) was carried out twice before transplantation (days −21 and −14) and three times after transplantation (days 30, 55 and 80). Only animals with stable pre-transplantational scores of >7 rotations per minute (average 11+/−2) were included in this study.

Figure 4:
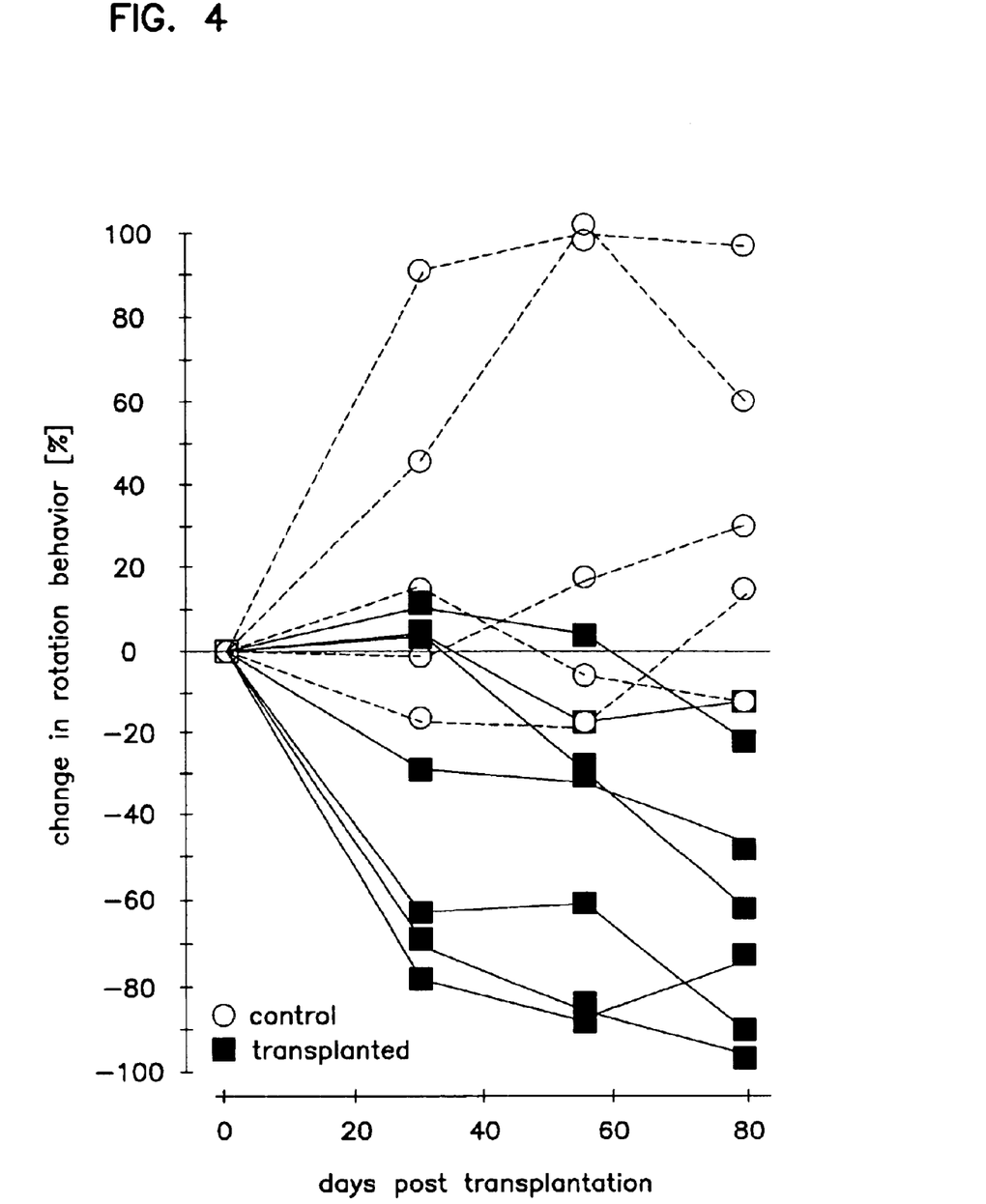
FIG. 4 is a graph showing the change in rotational behavior for rats receiving transplanted cells and control rats.

Gradual behavioral recovery was observed in transplanted animals (FIG. 4). Eight days post transplantation a substantial improvement in rotation scores could be detected in 5 out of 7 animals. The average reduction in rotation scores for these 5 animals was 75% as compared to pre-transplantation scores; range 47 to 97%). The remaining 2 animals showed only mild improvement (13% and 22% reduction). Control animals showed no behavioral improvement.

The survival rate of grafted dopaminergic neurons derived from expanded precursors was 3–5% demonstrating that long term survival and functional integration into the adult CNS can be achieved with expanded and pre-differentiated precursors.

The major pathological feature of Parkinson's disease is the loss of dopaminergic function in the substantia nigra. This pathology can be mimicked in non-human models of the disease by creating pharmacological or surgical lesions of the nitrostriatal dopaminergic pathway. The deficits in motor function that result from such lesions can be largely reversed when cell preparations made according to the invention are transplanted into the striatum of the lesioned animals. The degree of behavioral recovery in animals receiving transplants appears to be related to the number of dopaminergic neurons present in the grafted tissue. The improvement in animal behavior is most likely due to local dopamine release by the grafted cells.

B. Immunohistochemistry

Total graft volume was estimated using the Cavalieri's estimator as described by Gundersen et al. (1988) *APIMS* 96, 379–394. TH-ir cells were counted within the outlined graft area as used for volume estimation. Uniform randomly chosen sections of individual reaggregates were analyzed for the total number of TH-ir cells by means of a stereological grid (fractionator). Conventional and confocal images were obtained with Axiophot and Axiovert microscopes respectively (Zeiss). Confocal image stacks were acquired by single and dual wavelength excitation at 488 and 568 nm. Identically treated but non-BrdU incubated control cultures were used as a negative control for BrdU/TH double immunohistochemistry. Posttransplantational rotation scores were compared by the non-parametric Mann-Whitney U Test. The effect of serum and growth factors was analyzed using ANOVA and Dunnett posthoc comparisons. Data are given as mean+/−SEM.

Immunohistochemical analysis of the substantia nigra, ventral tegmental area and the striatum confirmed that all animals included in this study had a complete lesion. All animals had viable grafts 80–101 days after transplantation. The number of surviving TH-ir cells per graft was 1221+/−431 and the average graft volume was 0.92+/−0.12 mm$^3$ resulting in a TH-ir cell density of 1369+/−389 cells/mm$^3$. Graft size and TH-ir cell density in this study were similar to those found when transplanting primary fetal mesencephalic tissue (Spenger et al., (1996) *Exp.Brain Res.* 112, 47–57). A graft with only 478 surviving TH-ir cells and a more than 3 fold lower than average cell density was found in one of the two animals without significant behavioral recovery. The other animal with only mild behavioral improvement had an average number of surviving TH-ir cells but the graft was located ectopically. Cells in all of the grafts displayed morphological features of mature dopaminergic neurons and a strong immunoreactivity for TH (FIG. 4). These results show that grafted dopaminergic neurons derived from expanded precursors are functional in vivo and can alleviate behavioral deficits in an animal model for Parkinson's disease.

While the invention has been described in the above specification, examples and data, it is to be understood that the invention is not limited to the disclosed embodiments, but is intended to cover various modifications and equivalent arrangements included within the spirit and scope of the appended claims. All references cited herein are hereby incorporated by reference in their entirety.

What is claimed is:

1. A method of generating a cell culture comprising dopaminergic neuron cells, said method comprising the sequential steps of:
   a. providing precursor cells comprising human or rat fetal central nervous system cells;
   b. proliferating precursor cells, said step of proliferating comprising:
      i. incubating a suspension of said precursor cells in a proliferating medium which includes basic fibroblast growth factor (bFGF) to form proliferated precursor cells; and subsequently
   c. differentiating said proliferated precursor cells, said step of differentiating comprising:
      i. incubating said proliferated precursor cells in an incubation vessel which contains differentiation medium in a manner effective to form a reaggregation of differentiated dopaminergic neuron cells that is not adhered to any surface of the incubation vessel, wherein the differentiation medium includes ascorbic acid.

2. The method of claim 1, where said step of differentiating comprises incubating the precursor cells in a roller tube.

3. The method of claim 1, wherein said step of proliferating comprises plating said suspension of precursor cells onto a proliferating medium and incubating for 5 to 10 days.

4. The method of claim 3, wherein said suspension comprises $50\times10^3$ cells/ml to $500\times10^3$ cells/ml precursor cells.

5. The method of claim 1, wherein said step of differentiating comprises incubating said precursor cells in differentiation medium for 5 to 10 days.

6. The method of claim 1, wherein said cell culture comprises between 1% and 5% glial cells.

7. The method of claim 1, wherein said precursor cells comprise mesencephalic cells.

8. The method of claim 1, wherein said cell culture further comprises cholinergic neuronal cells.

9. The method of claim 8, wherein said precursor cells comprise basal forebrain cells or spinal cord cells.

10. The method of claim 1, wherein said cell culture further comprises serotonergic cells.

11. The method of claim 10, wherein said precursor cells comprise nucleus raphe cells.

12. A cell culture comprising a population of cells;
   about 80% to about 95% of the population of cells being differentiated neuronal cells;
   less than 5% of the population of cells being glial cells; and at least 9.9% of the population of cells being dopaminergic cells.

13. The cell culture of claim 12, wherein 18.4%+/−5.1% of the total cell population is dopaminergic neurons.

14. A method of treating a patient for Parkinson's disease, said method comprising administering cells produced according to the method of claim 1 to the patient to treat the patient for Parkinson's disease.

15. The method of claim 14, wherein the method of treating a patient further comprises:
   i. suspending said cells in a physiologically compatible carrier;
   ii. introducing a therapeutically effective amount of said cells into the brain of the patient.

16. The method of claim 15 wherein introducing a therapeutically effective amount further comprises administering $1-4\times10^6$ dopaminergic neurons, wherein administering further comprises loading said cells into a syringe and injecting them within the parenchyma of the patient's brain.

17. An assay for evaluating the effect of substances on differentiated neuronal cells, comprising:
   A. culturing differentiated neuronal cells, said step of culturing comprising:
      i. proliferating neuronal precursor cells, said step of proliferating comprising:
         a. incubating said neuronal precursor cells in proliferating medium which includes basic fibroblast growth factor (bFGF); and
      ii. differentiating said neuronal precursor cells, said step of differentiating comprising:
         aa. incubating said precursor cells in an incubation vessel which contains differentiation medium in a manner effective to form a reaggregation of differentiated cells that is not adhered to any surface of the incubation vessel, wherein said differentiating medium includes ascorbic acid,
   B. exposing said differentiated neuronal cells to the substance; and
   C. observing the effect of the substance on said differentiated neuronal cells.

18. The method of claim 1, wherein the precursor cells comprise human fetal cells obtained between about embryonic week 5 and about embryonic week 8.

19. The method of claim 1, wherein the precursor cells further comprise rat fetal cells obtained between about embryonic day 10 and about embryonic day 12.

20. The cell culture of claim 12, wherein about 15% to about 20% of the population of cells are dopaminergic cells.

21. The cell culture of claim 12, wherein about 15% of the population of cells are dopaminergic cells.

22. The cell culture of claim 12, wherein 14.1+/−4.2% of the population of cells are dopaminergic cells.

23. The cell culture of claim 12, wherein 9.9% to 23.5% of the population of cells are dopaminergic cells.

* * * * *